(12) United States Patent
Christenson et al.

(10) Patent No.: US 6,960,625 B2
(45) Date of Patent: Nov. 1, 2005

(54) TRANSPARENT POLYURETHANE-HYDROGEL COMPOSITION, METHOD OF MAKING TRANSPARENT POLYURETHANE-HYDROGEL COMPOSITION, AND AIR-FRESHENER APPLICATION

(75) Inventors: Christopher P. Christenson, Lake Jackson, TX (US); Stan Wrobel, West Newbury, MA (US); Deepak K. Sharma, Midland, MI (US); Joey W. Storer, Midland, MI (US); Andrew F. Sandford, Marlborough, MA (US)

(73) Assignee: Dow Global Technologies Inc., Midland, MI (US)

( * ) Notice: Subject to any disclaimer, the term of this patent is extended or adjusted under 35 U.S.C. 154(b) by 257 days.

(21) Appl. No.: 10/152,888

(22) Filed: May 21, 2002

(65) Prior Publication Data

US 2003/0105221 A1 Jun. 5, 2003

Related U.S. Application Data

(60) Provisional application No. 60/292,545, filed on May 21, 2001.

(51) Int. Cl.$^7$ .............................................. C08L 75/12
(52) U.S. Cl. ..................... 524/589; 524/839; 528/48; 528/59; 528/60; 528/61; 528/68
(58) Field of Search ................................ 524/589, 839, 524/800; 528/48, 59, 60, 61, 68, 44; 525/54.22, 458

(56) References Cited

U.S. PATENT DOCUMENTS

| | | | |
|---|---|---|---|
| 3,939,123 A | * 2/1976 | Matthews et al. | 528/60 |
| 4,209,605 A | * 6/1980 | Hoy et al. | 528/54 |
| 4,367,259 A | * 1/1983 | Fulmer et al. | 442/120 |
| 4,517,326 A | 5/1985 | Cordts et al. | 524/310 |
| 4,668,564 A | 5/1987 | Orchard | 428/246 |
| 5,060,858 A | 10/1991 | Santini | 239/60 |
| 5,462,536 A | 10/1995 | Braatz et al. | 604/304 |
| 5,756,632 A | * 5/1998 | Ward et al. | 528/28 |
| 6,039,266 A | 3/2000 | Santini | 239/60 |
| 2004/0029241 A1 | * 2/2004 | Hahn et al. | 435/174 |

FOREIGN PATENT DOCUMENTS

| | | |
|---|---|---|
| DE | 23 47 299 A1 | 10/1975 |
| EP | 0 426 422 A2 | 5/1987 |

OTHER PUBLICATIONS

MSDS for Polyethylene glycol taken from the internet site of JT Baker.*

Cordes et al., "Process Design for Large–Scale Purification of Formate Dehydrogenase from *Candida boidinii* by Affinity Partition," *J. of Chromatography*, vol. 376, pp. 375–384 (1986).

Okada et al., "[4] Polymerizable NAD Derivative and Model Enzyme Reactor with Recycling of Polyethylene Glycol–Bound NAD," *Methods in Enzymology*, vol. 136, pp. 34–45 (1987).

Urrutigoity et al., "Biocatalysis in Organic Solvents with a Polymer–Bound Horseradish Peroxidase," *Biocatalysis*, vol. 2, pp. 145–149 (1989).

* cited by examiner

*Primary Examiner*—Marc S Zimmer (57) ABSTRACT

A transparent polyurethane-hydrogel composition includes a reaction product in aqueous solvent of a prepolymer and a water-soluble crosslinker in the substantial absence of organic solvent, and such a composition can be prepared by admixing a prepolymer and a water-soluble crosslinker in aqueous solvent and in the substantial absence of organic solvent. A prepolymer is present in an amount of no greater than about 5 weight percent based on total weight of all hydrogel components. The prepolymer is generally prepared from at least one water-soluble polyol and an isocyanate. A water-soluble crosslinker generally has a crosslinker functionality of at least 2 and is selected to provide a site ratio of initial isocyanate to crosslinker (i.e., moles NCO× functionality/moles crosslinker×functionality) of at least about 1.5 and no greater than about 2.6. In one embodiment, a crosslinker is effective to react with and solubilize residual isocyanate concurrently with the reaction between prepolymer and crosslinker. A transparent polyurethane-hydrogel composition has desirable gel physical properties and is useful for an air-freshener application.

51 Claims, 3 Drawing Sheets

Figure 3

TRANSPARENT POLYURETHANE-HYDROGEL COMPOSITION, METHOD OF MAKING TRANSPARENT POLYURETHANE-HYDROGEL COMPOSITION, AND AIR-FRESHENER APPLICATION

This application claims the benefit of U.S. Provisional Application No. 60/292,545, filed May 21, 2001, which is hereby incorporated by reference.

FIELD OF THE INVENTION

The invention is directed to a transparent polyurethane-hydrogel composition and to a method for making a transparent polyurethane-hydrogel composition. More particularly, the invention is directed to a transparent polyurethane-hydrogel composition prepared from a prepolymer in an amount of no more than about 5 weight percent and a water-soluble crosslinker. A transparent polyurethane-hydrogel composition of the invention is particularly useful for applications containing fragrance compositions, particularly air-freshener applications.

BACKGROUND OF THE INVENTION

A polyurethane gel is created from a polyurethane network and a solvent. The polyurethane network envelops the solvent and can prevent the solvent from flowing out of the network. The properties of a polyurethane gel depend largely on the structure of the polyurethane network that makes up the gel and the interaction of the network and the solvent. The polyurethane network depends on the crosslink structure of the network, which depends on, for example, the amount and type of the reactants used to make the network and their ability to react to near completion. The polyurethane network can be important for determining the strength of the gel and can also be important for the diffusion of molecules through the tortuous path in the gel.

For some applications, one desirable characteristic of a polyurethane gel is transparency. Transparency is determined by the polyurethane network in combination with the solvent as well as the residual reactants. Thus, some reactants that may provide a desirable polyurethane network may be unable to provide transparency, and some reactants that can provide transparency may be unable to provide a desirable network.

A variety of polyurethane gels are known, and some of these gels are transparent. The known transparent polyurethane gels are less than desirable because they generally require large amounts of polymer—e.g., more than 5 weight percent and even more than 20 weight percent in some applications. Using such large amounts of polymer can be expensive and can negate or reduce transparency. These gels are also typically prepared in an organic solvent, which can be at least partly removed in a washing step after the gel is formed. This washing step can be slow and expensive in high-volume manufacturing applications.

Attempts to reduce the amount of polymer in known formulations to no more than 5 weight percent can adversely affect gel formation. And attempts to modify known formulations by altering the reactants such that less than 5 weight percent of polymer can form a desirable gel can adversely affect gel transparency.

Thus, it would be desirable to prepare a polyurethane gel by using a reduced amount of polymer as compared to known formulations while still obtaining a transparent gel and desirable physical properties. It would also be desirable to prepare a polyurethane gel in the substantial absence of volatile organic solvent, while still maintaining gel transparency.

SUMMARY OF THE INVENTION

According to the invention, a transparent polyurethane-hydrogel composition includes a reaction product of a prepolymer and a water-soluble crosslinker in water and in the substantial absence of organic solvent. Generally a composition of the invention is prepared by admixing at least one prepolymer and at least one crosslinker in aqueous solvent and in the substantial absence of organic solvent.

A prepolymer includes at least one water-soluble polyol and at least one isocyanate.

A water-soluble crosslinker generally has a functionality of at least 2 and is selected in a site ratio of isocyanate to crosslinker (i.e., moles NCO×functionality/moles crosslinker×functionality) of at least about 1.4 and no greater than about 2.7.

In one embodiment, a water-soluble crosslinker includes a polyamine having a charge density of at least 0.8 meq charge per gram of crosslinker.

In another embodiment, a water-soluble crosslinker includes polyethylenimine, which has a charge density of between about 20 and about 25 meq charge per gram of crosslinker.

In another embodiment, a water-soluble crosslinker includes at least one of a 3-arm end-capped polyethyleneglycol and polyoxyethylene bis(amine).

In yet another embodiment, a water-soluble crosslinker has a functionality effective to provide a reaction rate with said prepolymer that is at least 10 times faster than the reaction rate of water with said prepolymer.

In still another embodiment, a water-soluble crosslinker is selected to be effective to react with and solubilize residual isocyanate at least concurrently with the reaction between prepolymer and crosslinker.

In still another embodiment a crosslinker is chosen to be an amine end-capped polyethylene oxide or polyalkylene oxide.

A composition of the invention can be prepared by admixing a prepolymer in an amount of 5 weight percent and a water-soluble crosslinker in water and in the substantial absence of organic solvent.

A composition of the invention has a desirable physical gel property, particularly an effective number-average molecular weight between crosslinks. In one embodiment, the composition has a number-average molecular weight between crosslinks of at least about 2,000 and no greater than about 10,000.

In another embodiment, a composition has a tensile modulus of at least about 800 kPa and no greater than about 4000 kPa at 25° C.

A composition of the invention can be included in a fragrance-containing composition. One suitable fragrance-containing composition is an air-freshener composition. An air-freshener composition includes a prepolymer, a fragrance composition, and a water-soluble crosslinker.

A method of making a composition of the invention includes admixing at least one prepolymer and at least one water-soluble crosslinker in aqueous solvent and in the substantial absence of organic solvent to form a polyurethane-hydrogel mixture and polymerizing the mixture. The composition is substantially polymerized, is transparent, and has an effective number-average molecular weight.

BRIEF DESCRIPTION OF THE FIGURES

FIG. 1 represents compositions that have 2.7 weight-percent prepolymer, and FIG. 2 represents compositions that have 5 weight-percent prepolymer.

DETAILED DESCRIPTION OF THE INVENTION

The invention is directed to a transparent polyurethane-hydrogel composition and to a method for making a transparent polyurethane-hydrogel composition. A transparent polyurethane-hydrogel composition according to the invention is prepared from a prepolymer and a water-soluble crosslinker in an aqueous solvent and in the substantial absence of organic solvent.

The prepolymer is present in an amount effective to provide a polyurethane hydrogel with desirable gel physical properties and with transparency. Generally the prepolymer is present in an amount of no more than about 5 weight percent, preferably no more than about 4.5 weight percent, and preferably no more than about 4 weight percent. But the prepolymer is generally present in an amount of at least about 1 weight percent, preferably at least about 1.5 weight percent, more preferably at least about 1.7 weight percent, and still more preferably at least about 2 weight percent. In one embodiment, the prepolymer is present in an amount of between about 2.5 weight percent and about 3.5 weight percent.

A transparent polyurethane-hydrogel composition of the invention is useful for applications that contain fragrance compositions, particularly air-freshener applications.

The term "polymerized" or "polymerizing" means the composition is in the form of gel and does not flow under its own weight. This transformation from liquid components to polymer generally produces molar mass increase, network formation, phase separation, or a combination of these. When the composition does not substantially flow when the substrate is tipped, the composition is considered to be substantially polymerized. Generally the gel is effectively polymerized if a 100-ml container that includes a polyurethane-hydrogel composition can be inverted 180° and the composition does not flow out of the container (i.e., exhibits finite yield stress).

One advantage of the composition of the invention is that it is transparent. According to the invention, the term "transparent" means that a polyurethane-hydrogel composition of the invention is optically transparent. This means that a transparent polyurethane-hydrogel composition generally transmits light similar to how water transmits light at the same wavelength. Light transmittance can be determined by the Beer-Lambert Law $$\left[\ln\left(\frac{I_0}{I}\right) = -\varepsilon Cl\right],$$

where $\varepsilon$ is the specific molar absorptivity, I is the intensity of transmitted light, $I_0$ is the intensity of incident light, and l is the cell length, and C is the concentration of a light absorbing component.

Generally the term "transparent" means that a polyurethane-hydrogel composition of the invention transmits at least about 40 percent, preferably at least about 45 percent, and more preferably at least about 50 percent of light at 600 nanometers (nm) through a quartz cuvette having a cell pathlength of about 4 cm. One of skill in the art knows that transmittance varies with wavelength and pathlength and that 600 nm represents the middle of the visible spectrum, which ranges between 400 nm and 800 nm. One of skill in the art will also recognize that percent transmittance can be affected by adding a colorant to a composition of the invention. Transparency should be determined before adding a colorant or by choosing a wavelength of light that would transmit light without substantial interference of the colorant.

In one embodiment, a transparent polyurethane-hydrogel composition of the invention transmits at least about 1.5 times, preferably at least about 2 times, more preferably at least about 3 times, and still more preferably at least about 4 times more light at 600 nm through a quartz cuvette having a cell pathlength of about 4 cm than a gel composition prepared from a crosslinker (e.g., water, ethylene diamine, diethylene diamine, and triethylene triamine) other than a water-soluble crosslinker according to the invention. Such a comparison uses the same testing conditions—e.g., time, wavelength, cell thickness, and temperature—for each sample.

The percent transmission can be determined within at least about 36 hours of preparing a composition, preferably within at least about 24 hours of preparing a composition, and more preferably within at least about 12 hours of preparing a composition. Deionized water at about pH 7 can be used as the control.

A polyurethane hydrogel of the invention has physical gel properties suitable for its intended end-use application. These physical properties can be modified by selection of the amount and type of hydrogel components, particularly isocyanate, polyol, and water-soluble crosslinker.

One such property is crosslink density. Crosslink density affects the stiffness, tensile modulus, and compressive strength of a material. One of skill in the art is familiar with these relationships, but they will be briefly described here.

$$\text{Crosslink density} = \frac{\text{number of crosslinks}}{\text{polymer mass}} \qquad (1)$$

The molecular weight between crosslinks of a system, $M_c$, will also be related to the crosslink density of a system. $M_c$ is related to the density of the material by the approximation shown in Equation (2). This parameter is related to the Shear Modulus of the system via Equation (3) and to the Young's Tensile Modulus by Equation (4).

$$\rho \approx \frac{NM_c}{N_A} \qquad (2)$$

where:
N is the number of chains per unit volume
$N_A$ is Avogadro's number $$G = \rho \frac{RT}{M_c} \quad (3)$$

where:
G is the shear modulus
ρ is the density of the dry network (≈1 gm/cc)
R is the gas constant
T is the temperature and
$M_c$ is the average molecular weight between elastically effective crosslinks The Young's Tensile Modulus, E, is given by:

$$E = \frac{3\rho RT}{M_c} = 3G \quad (4)$$

One physical property is based on the number-average molecular weight between crosslinks ($M_c$). An effective $M_c$ provides support to a three-dimensional gel configuration and a substantially stable gel, and the $M_c$ generally is not so great or so low that a composition of the invention becomes unsuitable for its intended end-use application. A composition of the invention is unsuitable for its intended end-use application if, for example, a fragrance oil cannot diffuse out of the network of a polyurethane hydrogel to release fragrance.

The number-average molecular weight between crosslinks can be measured experimentally by swelling the gel and measuring the gel's change in volume-mass ratio. The value of number-average molecular weight between crosslinks can be controlled by varying the amount and molecular weight of prepolymer and the amount and molecular weight of water-soluble crosslinker. The nature of the gel and its internal topology can be varied, and even optimized, by simulation of gelation through the use of Monte Carlo gelation-simulation techniques. These techniques allow for an estimate of gel characteristics including such measures as the crosslink density of the network as well as the number-average molecular weight between crosslinks.

According to simulation techniques, a composition according to the claimed invention generally has an $M_c$ of at least about 2,000, preferably at least about 3,000, more preferably at least about 4,000, and still more preferably at least about 5,000. But the $M_c$ is generally no greater than about 8,000, preferably no greater than about 7,000, and more preferably no greater than about 6,000.

These $M_c$ values may be related to experimental observables—the tensile modulus. An effective tensile modulus for a composition of the invention is great enough to provide a shape suitable for an end-use application. For a composition of the invention, the tensile modulus can be difficult to measure due to its low value, but the tensile modulus can be reliably estimated from the number-average molecular weight between crosslinks.

Generally a transparent polyurethane hydrogel of the invention has a tensile modulus of at least about 800 kiloPascal (kPa), preferably at least about 1200 kPa, and more preferably at least about 1500 kPa at a temperature of about 25° C. Generally the modulus is no greater than about 4000 kPa, preferably no greater than about 3000 kPa, and more. preferably no greater than about 2000 kPa at a temperature of about 25° C.

Another physical property for a polyurethane hydrogel is gel strength. An effective gel strength is great enough to support a three-dimensional gel configuration and a substantially stable gel but not so great that a composition of the invention becomes unsuitable for its intended end-use application.

Gel strength can be determined by using a Stevens Texture Analyzer (available from Stevens Company) and a 0.5-inch Bloom Gelometer plunger (available from Stevens Company) as described in British Standard BS 757 (1975). Generally a polyurethane hydrogel has a gel strength of at least about 5 grams, preferably at least about 10 grams, and more preferably at least about 25 grams. But generally the gel strength is no greater than about 500 grams, preferably no greater than about 150 grams, and more preferably no greater than about 300 grams.

The term "desirable physical properties" means desirable values for number-average molecular weight between crosslinks, tensile modulus, or gel strength as described above.

Also according to the invention, the term "polyurethane" can refer to polyurethane, polyurea, or a mixture of polyurea and polyurethane. A polyurethane material can be obtained by a reaction of a polyol with an isocyanate. A polyurea material can be obtained by reaction of an amine with an isocyanate. A polyurethane material or a polyurea material can contain both urea functionality and urethane functionality, depending on the components included in a composition. Preferably a composition of the invention is a mixture of polyurethane material and polyurea material, which is generally known as a polyureaurethane. For purposes of this specification, no further distinction will be made between polyurethane and polyurea.

A composition of the invention is prepared in an aqueous solvent and in the substantial absence of an organic solvent. The terms "substantially free of organic solvent" and "substantial absence of organic solvent" mean an amount of organic solvent insufficient for dispersing hydrogel components to induce transparency in a polyurethane-hydrogel composition of the invention.

Generally the amount of organic solvent is no more than about 3 weight percent, preferably no more than about 2 weight percent, more preferably no more than about 1 weight percent, and even more preferably no more than about 0.5 weight percent. Still more preferably, the amount of organic solvent is no more than about 0.1 weight percent. Examples of organic solvents include acetonitrile, dimethyl formamide, dimethyl sulfoxide, tetrahydrofuran, dioxane, dichloromethane, acetone, and methyl ethyl ketone. The term "weight percent" is based on the total weight of the hydrogel components that are used to prepare a transparent polyurethane-hydrogel composition of the invention. The balance of all formulations is aqueous solvent.

The term "aqueous solvent" means any water-based solution suitable for dispersing hydrogel components such as sterile water, saline, and buffer.

The term "hydrogel component(s)" includes any component used to prepare a polyurethane-hydrogel composition of the invention such as isocyanate, polyol, water, water-soluble crosslinker, and additives, for example, a fragrance oil, a surfactant, an antioxidant, an antifreeze, a bittering agent, and other additives that can, for example, control fragrance release.

The term "composition" or "polyurethane-hydrogel composition" will be understood to one of skill in the art having read this specification. To form a gel-based formulation, hydrogel components are mixed together. Initially much of the components will be dispersed in solution, but as the components begin to react to completion (i.e., polymerize), a gel network having solvent molecules dispersed throughout the network will form. Thus, a "composition" of the invention includes a polymerized composition (i.e., the reaction product of hydrogel components when the gel network is formed), but the "composition" also includes a reaction mixture when the hydrogel components are initially introduced and before a network is substantially formed. The term "polyurethane hydrogel" can be used to specifically refer to a composition that is polymerized.

A composition of the invention is particularly useful for air-freshener applications.

Polyurethane-Hydrogel Composition

A polyurethane-hydrogel composition of the invention is prepared by admixing a prepolymer with a water-soluble crosslinker in an aqueous solvent and in the substantial absence of organic solvent. A composition of the invention generally includes a reaction product of at least one isocyanate, at least one polyol, and at least one water-soluble crosslinker in aqueous solvent.

These components are chosen such that upon preparing a polyurethane hydrogel of the invention, the polyurethane hydrogel is transparent and has desirable physical properties for the intended end-use application.

A composition of the invention can also include additives that are known to be useful in polyurethane-hydrogel compositions for intended end-use applications.

Prepolymer

A polyurethane-hydrogel composition of the invention includes a prepolymer. Any prepolymer suitable for preparing a transparent polyurethane-hydrogel composition can be used.

An effective amount of the prepolymer is generally great enough to result in a three-dimensional gel configuration but not so great that the resulting polyurethane hydrogel is not transparent according to the invention.

The prepolymer is generally present in an amount of no more than about 5 weight percent, preferably no more than about 4.5 weight percent, and preferably no more than about 4 weight percent. But the prepolymer is generally present in an amount of at least about 1 weight percent, preferably at least about 1.5 weight percent, and more preferably at least about 2 weight percent.

In one embodiment, the prepolymer is present in an amount of between about 2.5 weight percent and about 3.5 weight percent. In another embodiment, the prepolymer is present in an amount of about 3 weight percent.

A prepolymer suitable for use with the invention generally includes a reaction product of at least one water-soluble polyol and at least one isocyanate. One of skill in the art having read this specification would understand that isocyanates and polyols that promote water solubility of the prepolymer and that do not substantially adversely affect transparency of the composition would be desirable.

The term "polyol" refers to a compound that has two or more isocyanate-reactive functional groups per molecule. These functional groups include hydroxyl —OH), sulfhydryl (—SH); carboxyl (—COOH), and amino (—NHR, with R being hydrogen, an alkyl moiety of $C_1$ to $C_{10}$, or epoxy) groups. The functional group is preferably —OH. The term "polyol" includes diol.

A water-soluble polyol suitable for use in the invention includes polyoxyalkylene polyols or polyols made up of ethylene-oxide monomer units. For polyols made up of ethylene-oxide monomer units, at least 50 weight percent, preferably at least 60 weight percent, more preferably at least 70 weight percent, and still more preferably at least 90 weight percent of the units should be ethylene oxide. Even 100 weight-percent ethylene oxide-containing polyols can be used. These polyols can include up to about 25 weight-percent propylene-oxide monomer units.

The water-soluble polyol generally has an average molecular weight of at least about 2,000, preferably at least about 5,000, and more preferably at least about 7,000 gram/mole. But the molecular weight generally is no greater than about 30,000, preferably no greater than about 20,000, more preferably no greater than about 15,000, and still more preferably no greater than about 10,000 gram/mole. In one embodiment, the water-soluble polyol has a molecular weight of about 7,500 gram/mole.

Suitable polyols include diols such as a high molecular-weight polyethyleneglycol of the formula $H(OCH_2CH_2)_x OH$ where x is an average number such that the glycol has an average molecular weight of at least about 500, preferably at least about 1,000, and more preferably at least about 2,000 gram/mole. But the average molecular weight of the glycol generally is no greater than about 30,000, preferably no greater than about 20,000, more preferably no greater than about 15,000, and still more preferably no greater than about 10,000 gram/mole.

Preferably the polyol includes at least one triol (i.e., trihydroxy compound) and is synthesized using initiators such as glycerol, trimethylolpropane, and triethanolamine.

Other polyols having more than 3 functional groups are also suitable and can be synthesized using initiators such as sorbitol, erythritol, sucrose, and pentaerythritol. These initiators can be used to make polyoxyalkylene polyols as well as polyols made up of ethylene-oxide monomer units.

Suitable polyoxyalkylene polyols include polyols that have at least one oxyethylene, oxypropylene, or oxybutylene repeat unit. Examples include polyoxypropylene glycols (e.g., VORANOL P-2000 polyol and VORANOL P-4000 polyol, both trademarks of, and available from, The Dow Chemical Company); polyoxypropylene-oxyethylene glycols (e.g., DOWFAX DM-30 surfactant and SYNALOX 25 D-700 polyglycol, both trademarks of, and available from, The Dow Chemical Company); polyoxyethylene triols (e.g., TERRALOX WG-98 lubricant and TERRALOX WG-116 lubricant, both trademarks of, and available from, The Dow Chemical Company); polyoxypropylene-oxyethylene triols (e.g, VORANOL CP 1421, VORANOL CP 3001 polyol, and VORANOL CP 6001 polyol, all trademarks of, and available from, The Dow Chemical Company); and polyoxyethylene hexols (e.g., TERRALOX HP-400 lubricant, trademark of, and available from, The Dow Chemical Company).

Suitable polyols made up of ethylene-oxide monomer units include polyols made from initiators reacted with ethylene oxide.

Functionality of the polyol is effective to facilitate processability of a prepolymer of the invention. The functionality should not be so low that a composition of the invention can take an undesirable amount of time to gel. But the functionality should not be so high that it substantially adversely effects gel time, transparency, or physical properties of the polyurethane hydrogel.

According to the invention, a polyol can have a functionality of at least about 2, preferably at least about 3, more preferably at least about 4, and even more preferably at least about 5. Generally the functionality is no greater than about 10, preferably no greater than about 9, and more preferably no greater than about 8.

In one embodiment, the functionality is at least 3. In another embodiment, the functionality is between about 2 and about 5.

Preferably the polyol is a 7,000 molecular-weight triol copolymer of ethylene oxide (75%) and propylene oxide (25%) (e.g., PLURACOL 1123 polyol and PLURACOL VY polyol, both a trademark of, and available from, BASF, Mount Olive, N.J.).

A prepolymer according to the invention includes an isocyanate. One of skill in the art having read the specification would understand that the selection of the isocyanate will depend on such factors as the selection of the polyol, the degree of handling or shaping used to prepare the polyurethane-hydrogel composition, and the end-use application of the composition.

The isocyanate can be advantageously selected from at least one of an organic isocyanate or at least one of a multifunctional polyisocyanate. These include aliphatic isocyanates and cycloaliphatic isocyanates. Examples of aliphatic isocyanates and cycloaliphatic isocyanates include hexamethylene diisocyanate; trans, trans-1,4-cyclohexyl diisocyanate; 2,4-and 2,6-hexahydrotoluenediisocyanate; 4,4'-,2,2'-,2,4'-dicyclohexylmethanediisocyanate; 1,3,5-tricyanato cyclohexane; isophorone diisocyanate trimers; and isophorone diisocyanate. Preferably the isocyanate is isophorone diisocyanate.

Although less preferred because they can discolor over time, the isocyanate can also include aromatic isocyanates. Examples of aromatic isocyanates include toluene-2,4-diisocyanate; toluene-2,6-diisocyanate; commercial mixtures of toluene-2,4 and 2,6-diisocyanates; m-phenylene diisocyanate; 3,3'-diphenyl-4,4'-biphenylene diisocyanate; 4,4'-biphenylene diisocyanate; 4,4'-diphenylmethane diisocyanate; 3,3'-dichloro-4,4'-biphenylene diisocyanate; cumene-2,4-diisocyanate; 1,5-napthalene diisocyanate; p-phenylene diisocyanate; 4-methoxy-1,3-phenylene diisocyanate; 4-chloro-1,3-phenylene diisocyanate; 4-bromo-1,3-phenylene diisocyanate; 4-ethoxy-1,3-phenylene diisocyanate; 2,4-dimethyl-1,3-phenylene diisocyanate; 5,6-dimethyl-1,3-phenylene diisocyanate; 2,4-diisocyanatodiphenylether; 4,4'-diisocyanatodiphenylether benzidine diisocyanate; 4,6-dimethyl-1,3-phenylene diisocyanate; 9,10-anthracene diisocyanate; 4,4'-diisocyanatodibenzyl; 3,3'-dimethyl-4,4'-diisocyanatodiphenylmethane; 2,6-dimethyl-4,4'-diisocyanatodiphenyl; 2,4-diisocyanatostilbene; 3,3'-dimethoxy-4,4'-diisocyanatodiphenyl; 1,4-anthracenediisocyanate; 2,5-fluorenediisocyanate; 1,8-naphthalene diisocyanate; 2,6-diisocyanatobenzfuran; 2,4,6-toluene triisocyanate; p,p',p"-triphenylmethane triisocyanate; and polymeric 4,4'-diphenylmethane diisocyanate.

A composition of the invention generally includes isocyanate in an amount effective for providing a desirable tensile modulus or number-average molecular weight between crosslinks. This amount should not be so high that a prepolymer becomes unprocessable or so low that the tensile modulus or number-average molecular weight between crosslinks of a polyurethane hydrogel is substantially adversely affected.

A prepolymer according to the invention generally includes an isocyanate-to-hydroxyl (NCO/OH) site or group (i.e., moles NCO×functionality/moles crosslinker×functionality) ratio of at least about 2, preferably at least about 2.1, and more preferably at least about 2.2. But this ratio is generally no greater than about 4, preferably no greater than about 3, and more preferably no greater than about 2.5.

A prepolymer according to the invention is generally dispersed in aqueous solvent to form an aqueous prepolymer solution. An aqueous prepolymer solution desirably has a viscosity effective for processing a composition according to the invention. This solution can also contain additives that facilitate solubility of the prepolymer so long as the additives are not substantially incompatible with the components in a composition of the invention.

A prepolymer according to the invention can be prepared by methods known in the art and can be obtained commercially. Known methods for preparing a prepolymer according to the invention generally involve admixing a polyol with an isocyanate and heating the mixture to a temperature effective to facilitate the reaction between the polyol and isocyanate. Examples of prepolymers suitable for use according to the invention, as well as methods for making such prepolymers, are included in U.S. Pat. No. 5,462,536. One such prepolymer is Hypol G-50 hydrophilic polymer (a trademark of The Dow Chemical Company, Midland, Mich.), which is described in Example 1 of this specification. One of skill in the art will also appreciate that the age of a prepolymer (i.e., the amount of time that passes between initial formation of the prepolymer and when the prepolymer is incorporated into a polyurethane-hydrogel composition) may affect the molecular weight of the prepolymer, which in turn, may affect how a particular prepolymer affects a polyurethane-hydrogel composition of the invention. One of skill in the art will also readily recognize that it may be less preferred to use a prepolymer immediately after it is prepared (i.e., fresh prepolymer), and it may be preferred to allow the prepolymer to build some additional molecular weight before incorporating it into a composition of the invention. This phenomenon is known in the polymer field, and one of skill in the art can readily determine the optimal age of a prepolymer without undue experimentation.

Water-Soluble Crosslinker

A composition of the invention also includes a water-soluble crosslinker. A crosslinker suitable for use in the invention is selected to provide a desirable gel time for a polyurethane-hydrogel composition of the invention and to provide a transparent composition.

The term "gel time" means the time that elapses between the time when a prepolymer and a crosslinker are first mixed together in aqueous solvent and the time at which that mixture polymerizes. Gel time can vary depending on the amount and type of hydrogel components selected as well as on the reaction conditions such as pH and temperature. The gel time is not critical for the composition and method of the invention. A suitable gel time will depend on the end-use application. That is, the gel time should be sufficiently long to allow for dispensing of the composition but not so long that the process for making the composition becomes prohibitively expensive or unfeasible for commercial purposes. For some applications, the gel time at 25° C. is generally less than about 5 minutes, preferably less than about 4 minutes, and more preferably less than about 2 minutes.

A crosslinker can be selected based on its functionality and water solubility. Generally a crosslinker should have a functionality (both number and type) that provides a reaction rate with the prepolymer that is at least 10 times faster than the reaction rate of water with the prepolymer. And the functionality preferably provides a reaction rate that is at least 100 times faster, more preferably at least 1,000 times faster, even more preferably at least 10,000 times faster, and still more preferably at least 100,000 times faster than the reaction rate of water with the prepolymer.

A crosslinker generally has a functionality of at least 2, preferably at least 3, more preferably at least 4, still more preferably at least 5, and even more preferably at least 6. But a crosslinker generally has a functionality of no more than about 40, preferably no more than about 30, and more preferably no more than about 20. In one embodiment, a crosslinker has a functionality of at least about 8 and no more than about 16. The term "functionality" is known to one of skill in the polyurethane art and generally refers to the number of active hydrogens per molecule able to react with the unreacted isocyanate groups of the prepolymer. The functionality generally provides about 2 or more active hydrogen groups per molecule. The active hydrogen groups can be hydroxyl, mercaptyl, or amino groups.

The site or group (i.e., moles NCO×functionality/moles crosslinker×functionality) ratio of initial isocyanate to crosslinker is generally at least about 1.4, preferably at least about 1.6, and more preferably at least about 1.8. But this ratio is generally no greater than about 2.7, preferably no greater than about 2.4, and more preferably no greater than about 2.1.

The combination of functionality and water solubility of a crosslinker is selected to provide a polyurethane hydrogel of the invention with a desirable tensile modulus or number-average molecular weight between crosslinks and transparency.

It has surprisingly been found that the selection of the crosslinker is important to obtaining a transparent polyurethane hydrogel of the invention. Although this invention is not limited to any particular theory, it is believed that the selection of crosslinker according to the invention facilitates solubility of the polyurethane network as well as serving to scavenge residual isocyanate. As a result, selection of crosslinker facilitates maintaining an aqueous phase and helps prevent formation of an insoluble phase that may arise from a nonuniform distribution of crosslinks.

The term "residual isocyanate" means that amount of isocyanate that did not react in the formation of the prepolymer. That is, "residual isocyanate" means that amount of isocyanate that is still available for reaction after a prepolymer is formed. It is believed that residual isocyanate can react with water and contribute to formation of an insoluble phase, thereby adversely affecting transparency.

According to the invention, the site or group (i.e., moles NCO×functionality/moles crosslinker×functionality) ratio of residual isocyanate to initial crosslinker functionality is no greater than about 0.8, preferably no greater than about 0.7, and more preferably no greater than about 0.6. In one embodiment, this ratio is between about 0.4 and about 0.5. In another embodiment, this ratio is about 0.47.

A crosslinker is present in an amount effective to form a network with the prepolymer and to scavenge or solubilize enough residual isocyanate to prevent formation of an insoluble phase, which substantially adversely affects transparency. A crosslinker should not be included in so large of an amount that it substantially adversely affects gel formation. The amount of crosslinker suitable for use with the invention will typically depend on the type of crosslinker selected and the prepolymer. One of skill in the art having read this specification would understand how to determine the amount of crosslinker suitable for the invention such that gelation occurs and the resulting polyurethane hydrogel has strength suitable for its end-use application.

In one embodiment, a crosslinker is solubilized in aqueous solvent, preferably water, to form a crosslinker solution. To control reactivity between a crosslinker and a prepolymer, the pH of the crosslinker solution can be controlled to promote reaction with prepolymer. For example, the pH of a 1 weight-percent solution of an amine-functionalized crosslinker (e.g., polyethylenimine) generally is at least about 7, preferably at least about 7.4, and more preferably at least about 7.8. But the pH generally is no greater than about 9.5, preferably no greater than about 8.6, and more preferably no greater than about 8.2. The pH of, for example, polyethylenimine can be controlled by addition of an acid, such as hydrochloric acid.

In one embodiment, the pH of a 1 weight-percent solution of an amine-functionalized crosslinker is about 8. The effective pH will depend on the type of crosslinker used. One of skill in the art having read this specification will recognize that any desirable pH control of the crosslinker solution will be unnecessary if a composition of the invention is prepared in an aqueous solvent that contains a pH buffer or some other pH control.

Examples of suitable crosslinkers include polyamines, amine end-capped polyols, polyols, and amine end-capped ethylene-oxide sugars.

Polyamines suitable for use with the invention have at least about 0.8 milliequivalent (meq) charge per gram of crosslinker. Suitable polyamines can have a charge density much higher than 0.8 meq charge per gram.

In one embodiment, a polyamine has 1.0 meq charge per gram, and in another embodiment, a polyamine has between 20 and 25 meq charge per gram. Suitable polyamines generally have a molecular weight of at least about 140 gram/mole, preferably at least about 170 gram/mole, and more preferably at least about 200 gram/mole. But suitable polyamines generally have a molecular weight no greater than about 2,000 gram/mole, preferably no greater than about 1,800 gram/mole, and more preferably no greater than 1,500 gram/mole.

In one embodiment, the polyamine is polyethylenimine having a molecular weight between about 600 gram/mole and about 800 gram/mole. Other molecular weights of polyethylenimine are also useful with the invention.

Polyols and amine end-capped polyols suitable for use with the invention are water soluble. Preferably they are ethylene-oxide based. Examples of polyamines include polyethylenimine (e.g., 600, 800, and 1200 molecular weight; e.g., CAS No. 25987-06-8), polyvinyl amine, and chitosan.

Although less preferred, other amine end-capped polyols include the water-soluble JEFFAMINE T-Series amines (e.g., JEFFAMINE T-403 [CAS 39423-51-3], which is a polyoxypropylenetriamine having an average molecular weight of approximately 440) and the JEFFAMINE ED-2003 amine [CAS 65605-36-9], which is a water-soluble aliphatic diamine derived from a propylene oxide-capped poly(ethylene oxide) with an approximate molecular weight of 2000 (trademark of, and available from, Huntsman, Austin, Tex.). The functionality of an amine end-capped polyalkyleneoxide may be increased by initiating polymerization with a sugar (e.g., polyacrylic acid, sorbitol, sucrose, erythritol, and pentaerytheratol).

Examples of polyols include VORANOL RN-482 polyol (trademark of, and available from, The Dow Chemical Company) and VORANOL CP-450 polyol (trademark of, and available from, The Dow Chemical Company).

Water-soluble crosslinkers such as 3-, 4-, 5-, and higher functional amine end-capped polyethylene glycols should have sufficient molecular weight such that upon incorporation into a polyurethane hydrogel, the Mc is at least about 2,000, preferably at least about 3,000, more preferably at least about 4,000, and still more preferably at least about 5,000. But the $M_c$ should be no greater than about 8,000, preferably no greater than about 7,000, and more preferably no greater than about 6,000.

Another exemplary crosslinker includes multifunctional amine end-capped ethyleneoxides. One such crosslinker is shown here (I) and is a 4-functional poly(oxy-1,2- ethanediyl, α-hydroxy-ω-(2-aminoethoxy)-, ether with 2,2-bis(hydroxymethyl)-1,3-propanediol (4:1) (9C1)[CAS 169501-65-9], where n, which is the degree of polymerization in the structure below, can vary per chain but, in the end, typically corresponds to a final molecular weight of between about 484 and 1,189 grams/mole. Typically n can range from n=1 to n=5.

(I)

Other examples of amine end-capped poly(ethylene oxide) crosslinkers having a functionality of 2 to 12 can be found in the literature and include CAS Registry numbers 177986-99-1P; 179189-24-3; 52379-15-4; 244235-34-5; 244235-35-6; 244235-36-7; 244235-38-9; 172355-14-5; 180273-44-3; and 158948-29-9. Mono-, di-, and multifunctional polyalkylene oxides including poly(ethylene oxide) or polyethylene glycol are commercially available from Shearwater Polymers, Inc. (Huntsville, Ala.; e.g., Shearwater Corporation catalog number 0J2V0L13). One of skill in the art having read this specification can easily imagine derivatives of these crosslinkers that would also be useful for the invention and such derivatives are considered to be within the scope of this invention. These types of compounds have been described in, for example, Urrutigoity and Souppe, *Biocatalysis*, 2:145 (1989); Cordes and Kula, *J. Chromat.*, 376:375 (1986); and Okada and Urabe, *Meth. Enzymol.*, 136:34 (1987) for uses other than as described for this invention, but they have surprisingly been found to be useful for this invention.

One of skill in the art having read this specification will readily be able to select the type and amount of water-soluble crosslinker useful according to the invention.

Additives

A composition of the invention can also include known additives and other known components to prepare a polyurethane-hydrogel composition. Generally any additive known to one of skill in the art to be useful in preparing a transparent polyurethane-hydrogel composition can be included in a composition of the invention so long as the additive is not substantially incompatible with other components in the composition and so long as the additive does not substantially adversely affect the transparency of the composition.

Examples of additives include antioxidants, surfactants, and antifreezes.

Suitable surfactants are effective to solubilize hydrogel components or other additives and include TRITON X-100 surfactant, TRITON X-102 surfactant (Union Carbide Corporation), and DOWFAX 63N40 surfactant (The Dow Chemical Company, Freeport, Tex.).

Suitable antifreezes are effective to facilitate freeze stability of a composition of the invention and include methanol, ethanol, ethylene glycol, and isopropyl alcohol. If any antifreeze is added and such an antifreeze can be considered an organic solvent, the amount should be small enough such that no more than a trace amount of organic solvent is introduced into the composition and certainly substantially less than an amount that would disperse hydrogel components.

The balance of a composition of the invention is water. The amount of water can vary depending on the intended end-use application.

Method

A method of the invention includes admixing a prepolymer, and a water-soluble crosslinker in an aqueous solvent and in the substantial absence of organic solvent. The hydrogel components are admixed in a manner effective to disperse the hydrogel components in water. According to the invention, the method is carried out substantially free of organic solvent. One of skill in the art having read this specification would understand that conventional mixing methods can be used to disperse the prepolymer in water.

Additives can be included in a composition of the invention at any time during the method. For example, an additive can be dispersed with a prepolymer in aqueous solvent to form a prepolymer solution, which can be subsequently admixed with a water-soluble crosslinker. As another example, an additive can be dispersed with a water-soluble crosslinker to form a crosslinker solution, which can be subsequently admixed with a prepolymer to form a composition of the invention.

The conditions are generally selected such that they are not substantially incompatible with hydrogel components. These conditions can be selected without undue experimentation by one of skill in the art having read this specification. These conditions, for example, temperature, pH, and mixing, will vary depending on the hydrogel components selected and the intended end-use application.

Also according to the invention, the reaction mixture can be deposited onto a substrate during any step. For example, all hydrogel components can be admixed and the mixture can be deposited into a container. Alternatively, the prepolymer can be deposited into a container and then polymerized with crosslinker.

The following description provides one example of a method of the invention. To prepare a polyurethane-hydrogel composition of the invention, a prepolymer can be dispersed in aqueous solvent. One of skill in the art having read this specification would understand that conventional mixing methods can be used to disperse the prepolymer in aqueous solvent.

Next, a crosslinker solution can be added to the prepolymer, and the mixture can be stirred for an amount of time effective to disperse hydrogel components in aqueous solvent. Again, one of skill in the art having read this specification would understand that conventional mixing methods can be used.

The composition can then be deposited into a container suitable for an intended end-use application.

In one embodiment, 100 ml of a mixture of the prepolymer and crosslinker are mixed for about 15 seconds using a mechanical stirrer.

The gel time for a composition of the invention desirably allows effective processing and dispensing of the composition.

In one embodiment, the crosslinker solution is added to the prepolymer in a container suitable for holding a polyurethane-hydrogel composition of the invention. In this embodiment, the gel time can be as fast as ½ second at room temperature (25° C.).

In another embodiment, the crosslinker solution is added to the prepolymer in a first container and then subsequently poured into a second container suitable for holding a polyurethane-hydrogel composition of the invention. In this embodiment, the gel time can be as long as, for example, 30 minutes but can also be longer.

Suitable containers for holding an air-freshener composition of the invention include any container that does not substantially adversely interact with the composition of the invention, e.g., glass jar, plastic container, and ceramic container. Preferably the container takes advantage of the transparency of the composition.

Other suitable containers will depend on the end-use application.

Air-Freshner Application

One application for a transparent polyurethane-hydrogel composition of the invention includes an application that contains a fragrance composition. Fragrance compositions are known for their use in air-freshener compositions.

Traditionally air-freshener compositions have been valued for imparting a desirable scent to the air to mask stale or unpleasant odors. The containers used for air-freshener compositions have tended to be more functional rather than aesthetically pleasing. More recently, though, air-freshener compositions have been used to enhance a room's decor or ambiance. Thus, it is desirable for an air-freshener composition to be aesthetically pleasing, to harmonize with, or even enhance, room decor.

One way to meet this need is to provide a transparent air-freshener composition. Transparent air-freshener compositions are known, but these compositions are typically made from gums, for example, carrageenates, alginates, pectins, or gelatin. But gum-based air-freshener compositions have several disadvantages.

One disadvantage of gum-based compositions is that the gel shrinks in a manner that is not proportional to the external dimensions. This shrinkage can affect the liberation of fragrance or fragrance release, can be visually unappealing, and is, therefore, undesirable. Particularly unattractive shrinking occurs when fragrance compositions based on gum-based gels are left uncovered and exposed to air.

Another disadvantage of gum-based compositions is that they have less than desirable heat stability. These gels can begin to flow at temperatures as low as 40° C., depending on the nature of the gel network and the nature and composition of the gel. This can cause problems with transporting gels as well as using gels in warm climates. Thus, air-freshener compositions prepared from a polyurethane-hydrogel composition of the invention can be particularly advantageous—it not only can provide improved shrinkage and heat stability as compared to gum-based gels, but the composition of the invention can provide the aesthetically appealing transparency character and desirable gel strength.

An air-freshener composition can be prepared from a transparent polyurethane-hydrogel of the invention by admixing a prepolymer, a fragrance composition, and a water-soluble crosslinker in aqueous solvent and in the substantial absence of organic solvent.

A prepolymer suitable for use in the invention includes a prepolymer as described above, which is prepared as described above. The prepolymer generally includes a reaction product of at least one water-soluble polyol and at least one isocyanate.

A fragrance composition includes at least a fragrance oil but generally includes a fragrance oil, a surfactant, and water. Any fragrance oil suitable for preparing an air-freshener composition can be used. Generally the fragrance oil is selected so that its bright, effervescent top notes are balanced with its heart, which is also known as its middle note. The vapor pressure of a fragrance oil suitable for use in an air-freshener composition at 20° C. generally does not exceed 0.1 mm Hg. Examples of fragrance oil suitable for use in the invention include Berry Medley (Wessel Fragrance Inc., Anglewood Cliff, N.J.) and Grape Fragrance (Flavor and Fragrance Specialities, Mahwah, N.J.).

The amount of fragrance oil should not be so low that the scent is too mild, and the amount of the fragrance oil should not be so high as to make the manufacture of the air freshener prohibitively expensive. The amount of fragrance oil is generally at least about 2.5 weight percent, preferably at least about 3.0 weight percent, and more preferably at least about 3.5 weight percent. But the amount of fragrance oil is generally no more than about 5.0 weight percent, preferably no more than about 4.5 weight percent, and more preferably no more than about 4.0 weight percent.

Because fragrance oil is generally insoluble in aqueous solvents, to incorporate a fragrance oil into an aqueous solvent, the fragrance oil can be formulated with a surfactant. Any surfactant suitable for solubilizing a fragrance oil in an aqueous solvent is suitable for use in the invention. The surfactant is generally chosen such that it does not substantially adversely affect the transparency of a polyurethane-hydrogel composition of the invention.

Examples of suitable surfactants include a nonionic surfactant such as ethoxylated alkyl phenol (e.g., TRITON X-100 and TRITON X-102, both available from Union Carbide Corporation), nonyl phenols, and ethoxylated alcohols (e.g., DOWFAX 63N40 available from The Dow Chemical Company, Freeport, Tex.).

The surfactant is present in an amount effective for solubilizing the fragrance oil in an aqueous solvent. The amount of surfactant should not be so low that the transparency of the gel is substantially adversely effected, and the amount of surfactant should not be so high that the air-freshener composition becomes prohibitively expensive to manufacture. Generally the amount of surfactant should be no more than about 15 weight percent, preferably no more than about 12 weight percent, and more preferably no more than about 10 weight percent. In one embodiment, the surfactant is present in an amount between about 7 weight percent and about 8 weight percent.

The type and amount of surfactant generally depends on the type and amount of fragrance oil used. Thus, the selection of surfactant and fragrance oil is generally interdependent. One of skill in the art having read this specification would understand how to mutually choose effective surfactant and fragrance oil.

The fragrance composition can be prepared by essentially titrating fragrance oil in an aqueous solvent with surfactant. That is, surfactant can be added to an aqueous solvent of fragrance oil until the solution becomes transparent.

A fragrance composition can also include one or more additives. Generally any additive known to one of skill in the art to be useful in preparing a fragrance composition can be included in a composition of the invention so long as the additive is not substantially incompatible with other components in the composition. Examples of additives include antifreeze, antioxidant, bittering agent, and colorant.

One desirable additive includes an antifreeze. Examples of suitable antifreeze include methanol, ethanol, ethylene glycol, and isopropyl alcohol. An antifreeze can be selected to enhance fragrance release and can also aid freeze stability during, for example, transportation or storage of an air-freshener composition.

The amount of antifreeze should not be so high as to make the fragrance composition prohibitively expensive to manufacture or so high that the antifreeze disperses the prepolymer. The antifreeze is generally present in an amount of at least about 0.5 weight percent, preferably at least about 1.0 weight percent, and more preferably at least about 1.5 weight percent. But the antifreeze is generally present in an amount of no greater than about 5 weight percent, preferably no greater than about 4.0 weight percent, and more preferably no greater than about 3.0 weight percent.

Another desirable additive includes a colorant. Examples of suitable colorant include any water-based colorant such as food coloring and Reactint polymeric colorant (available from Milliken Chemical, Spartanburg, S.C.).

A polyurethane-hydrogel composition of the invention is transparent as already described above. When a colorant is added to the composition of the invention, the intent is to not substantially alter the composition's transparency, but all colorants necessarily absorb some amount of light at a particular wavelength that corresponds to that color. Thus, a composition of the invention has a transparency as described above in the absence of a colorant, but a colorant in the composition can substantially alter the transmission of light especially allowing for the transmission of light in a narrow range of wavelength.

To prepare an air freshener from a transparent polyurethane-hydrogel composition of the invention, a fragrance composition including water, fragrance, and surfactant is generally mixed using methods known to one of skill in the art until all components are dissolved. Next, a prepolymer is added to the mixed fragrance composition. The prepolymer and fragrance oil composition can also be mixed using methods known to one of skill in the art. In one embodiment, the prepolymer and the fragrance composition are mixed using a jiffy mixer (available from Aldrich, Milwaukee, Wis.) for an amount of time to disperse reactants in water. In one embodiment, the reactants are mixed for about 4 minutes.

A water-soluble crosslinker can then be added to the mixture of prepolymer and fragrance composition. The water-soluble crosslinker can be added alone or in aqueous solvent (e.g., in water). This mixture is stirred using methods known to one of skill in the art for an amount of time effective to disperse the components in water. In one embodiment, this mixing is done for about 15 seconds.

The gel time for an air-freshener composition desirably allows for effective processing and dispensing of the composition.

In one embodiment, the water-soluble crosslinker is added to the mixture of prepolymer and fragrance component in a container suitable for holding an air-freshener composition prepared from a transparent polyurethane-hydrogel composition of the invention. In this embodiment, the gel time can be as fast as ½ second at room temperature (25° C.).

In another embodiment, the water-soluble crosslinker is added to the mixture of prepolymer and fragrance component in a first container and then subsequently poured into a second container suitable for holding an air-freshener composition prepared from a transparent polyurethane-hydrogel composition of the invention before the composition polymerizes. In this embodiment, the gel time can be as long as 30 minutes but can also be longer at room temperature and 1 atmosphere pressure.

Suitable containers for holding an air-freshener composition of the invention include any container that does not substantially adversely interact with the composition of the invention, e.g., glass jar, plastic container, and ceramic container. The performance of an air-freshener composition will depend on the shape and design of the container as well as on the amount of, and hydrogel components used in, the polyurethane hydrogel. One of skill in the art having read this specification will readily be able to select a desirable container in combination with selection of hydrogel components.

An air-freshener composition according to the invention can also have a gel object suspended within the air-freshener composition while maintaining the transparency, texture, and structure of the transparent polyurethane-hydrogel of the air freshener. The gel object can be prepared from a variety of known gels such as gum-based gels and thermally-cured gels. But a preferred embodiment includes a gel object prepared from a transparent polyurethane-hydrogel composition of the invention. The gel object can be prepared in a variety of shapes such as fruit, animals, hearts, leaves, and stars by forming gel objects in molds. Examples of molds include candy molds, soap molds, and ice-cube trays.

Gel objects can be removed from the molds after a time period effective for the gel object to have sufficient stability to withstand demolding.

The gel object can be placed into containers suitable for holding an air-freshener composition made from a polyurethane-hydrogel composition, such as a glass jar, plastic container, and ceramic container, and the mixture of the prepolymer and the crosslinker can be added to the container that contains the gel object.

One advantage of using a transparent polyurethane-hydrogel composition in this application is that the hydrogel is processed at room temperature and is not thermally formed, which allows for the integrity of the gel object to be maintained when the transparent polyurethane-hydrogel composition is added to the container.

Another advantage of a transparent polyurethane-hydrogel composition in this application is that a gel object made by a transparent polyurethane-hydrogel does not have the shrinkage problems typically found with gum-based gels. As a result, the gel object can maintain its dimensional shape even when the air-freshener composition begins to shrink when water and fragrance oil evaporate.

An air-freshener composition can include other suspended objects that are advantaged by the composition's transparency such as glitter or confetti.

A gel object can be transparent but need not be transparent. In one embodiment, a gel object contains a pigment additive and is opaque or less than transparent.

The invention will be further described by the following Examples. These Examples are not meant to limit the invention but to further illustrate embodiments of the invention. Any reference to prepolymer in the Examples refers to the prepolymer in Example 1, unless the Example expressly states otherwise, and any reference to polyethylenimine (PEI) in the Examples refers to polyethylenimine having an average molecular weight of about 800 as first described in Example 2, unless the Example expressly states otherwise.

EXAMPLES

Example 1

Preparation of a Prepolymer Suitable for Use in the Invention

To prepare one example of a prepolymer suitable for use with the invention, a 7000 molecular-weight triol copolymer of ethylene oxide (75%) and propylene oxide (25%) (PLURACOL 1123 available from BASF, Mount Olive, N.J.) ("the polyol") was dried. Phosphoric acid (20 ppm) was added to the polyol. Next, the polyol (1687.46 g) was mixed with 165.0 g isophorone diisocyanate (IPDI) (available from Bayer, Pittsburgh, Pa.) and heated at 70° C. under dry nitrogen. Isocyanate levels were determined by addition of dibutylamine and back titration with standard acid. Fourteen days were required for the isocyanate concentration to reach 0.47 meq/g (0.39 meq/g=theoretical) according to ASTM No. D5155-96. The resulting prepolymer was liquid at room temperature (25° C.). This prepolymer is available from The Dow Chemical Company (HYPOL G-50 hydrophilic polymer).

Example 2
Determination of Transmittance of a Polyurethane-Hydrogel Composition of the Invention To determine the transmittance of a polyurethane-hydrogel composition of the invention, a polyurethane-hydrogel composition was prepared with the prepolymer of Example 1 according to the following formulations. A formulation of the invention (Invention Formulation) was compared to two comparative formulations. The first comparative formulation (Formulation 1) did not contain a crosslinker—only water—and the second comparative formulation (Formulation 2) did contain a crosslinker but not a crosslinker as defined for the invention. Table 1 shows the formulations used to make a composition that contains about 5 weight-percent prepolymer, and Table 2 shows the formulations used to make a composition that contains about 3 weight-percent prepolymer.

TABLE 1

Formulations for Composition With About 5 Weight-Percent Prepolymer

| Component | Formulation 1 (weight percent) | Formulation 2 (weight percent) | Invention Formulation (weight percent) |
|---|---|---|---|
| Water | 95 | 94.96 | 94.8 |
| Prepolymer | 5.0 | 5.0 | 5.0 |
| Polyethylenimine | — | — | 0.2 |
| Ethylene Diamine | — | 0.04 | — |
| pH | Neutral | 10.0 | 7.7 |

TABLE 2

Formulations for Composition With About 2.7 Weight-Percent Prepolymer

| Component | Formulation 1 (weight percent) | Formulation 2 (weight percent) | Invention Formulation (weight percent) |
|---|---|---|---|
| Water | 97.3 | 97.28 | 97.2 |
| Prepolymer | 2.7 | 2.7 | 2.7 |
| Polyethylenimine | — | — | 0.1 |
| Ethylene Diamine | — | 0.02 | — |
| pH | Neutral | 11.7 | 8.5 |

The prepolymer was prepared as described in Example 1. Polyethylenimine has an average molecular weight of about 800 and was obtained from Aldrich, Milwaukee, Wis. Ethylene diamine was obtained from The Dow Chemical Company, Freeport, Tex.

For each formulation, the prepolymer was first dispersed in water to form a prepolymer solution. For Formulation 1, all water was added to the prepolymer. For Formulation 2 and Invention Formulation, essentially all of the water was added to the prepolymer. The water and prepolymer were mixed in a 100 ml beaker by a mechanical stirrer for about 4 minutes.

For Formulation 2 the ethylene diamine crosslinker was added at 0.04 and 0.02 weight percent as shown in Tables 1 and 2 respectively. And for the Invention Formulation, a crosslinker solution of 1 weight percent was prepared and aliquoted into the prepolymer to provide the weight percent of crosslinker shown in Tables 1 and 2.

The pH of the crosslinker solution for Formulation 2 was adjusted to about 11.7 (2.7 weight-percent prepolymer) and to about 10.0 (5.0 weight-percent prepolymer) by the addition of concentrated hydrochloric acid. The pH of the crosslinker solution for Invention Formulation was adjusted to about 8.5 (2.7 weight-percent prepolymer) and to about 7.7 (5.0 weight-percent prepolymer) by the addition of concentrated hydrochloric acid.

For Formulation 2 and Invention Formulation, the prepolymer solution and crosslinker solution were admixed by use of a mechanical stirrer for about 15 seconds at 200 rpm.

Formulation 1 was still not polymerized after 24 hours. The approximate gel time for Formulation 2 was about 75 seconds (2.7 weight-percent prepolymer) and about 180 seconds (5.0 weight-percent prepolymer). And the approximate gel time for Invention Formulation was about 55 seconds (2.7 weight-percent prepolymer) and about 120 seconds (5.0 weight-percent prepolymer).

Each formulation was evaluated for its percent transmittance about 24 hours after the hydrogel components were mixed. Each formulation was evaluated using a cuvette having a path length of about 4 cm.

Formulation 1 (2.7 weight-percent prepolymer) showed a transmittance of about 0 percent at 600 nm relative to deionized water. Formulation 1 (5.0 weight-percent prepolymer) showed a transmittance of about 0 percent at 600 nm relative to deionized water.

Figure 1:
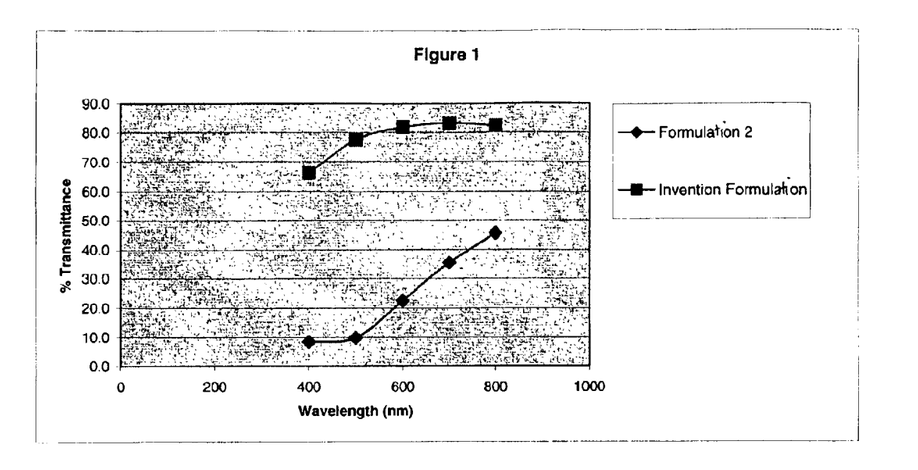
FIGS. 1 and 2 show the percent transmittance of a composition of the invention and a comparative composition over the visible range of 400 nm to 800 nm.
Figure 2:
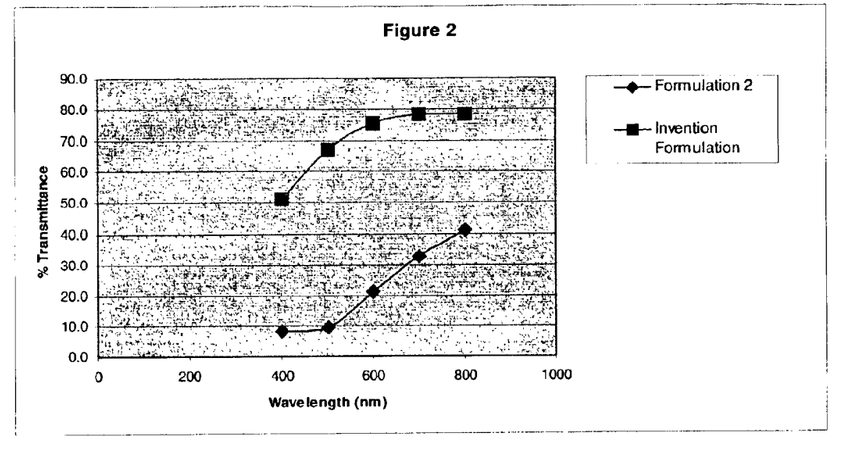

The results for Formulation 2 and Invention Formulation are shown in FIGS. 1 and 2. These Figures show percent transmittance of a sample in the visible spectrum from 400 to 800 nanometers (nm).

FIG. 1 shows percent transmittance of formulations made with 2.7 weight percent of prepolymer. Formulation 2 showed a percent transmittance of 21 percent at 600 nm. And Invention Formulation showed a percent transmittance of 81 percent at 600 nm.

FIG. 2 shows formulations made with 5 weight percent of prepolymer. Formulation 2 showed a percent transmittance of 21 percent at 600 nm. And Invention Formulation showed a percent transmittance of 76 percent at 600 run.

Example 3
Preparation of an Air-Freshener Composition According to the Invention To prepare an air-freshener composition according to the invention, the prepolymer of Example 1 was first prepared.

Next, a fragrance composition was prepared by admixing 3 g fragrance oil (Berry Medley available from Wessel Fragrance Inc., Anglewood Cliff, N.J.), 2 g ethanol, 7 g TRITON X-100 (available from Union Carbide Corporation), and 75 g water in a 250 ml beaker using a mechanical stirrer until all components were dispersed. This took about 30 minutes. The prepolymer (3 g) was then added to this mixture, and the components were mixed for an additional 4 minutes.

A crosslinker solution was prepared by dissolving 1 weight percent of polyethylenimine in 100 grams of water. The pH of the crosslinker solution was adjusted to about 9 by adding concentrated hydrochloric acid. The crosslinker solution was then added to the mixture containing the prepolymer by adding 10 g of the 1% polyethylenimine solution. All components were then mixed for about 15 seconds. After 60 seconds, a considerable increase in viscosity was observed. The gel time was about 80 seconds.

The air-freshener composition in this Example included 2.5 weight-percent prepolymer, 85.4 weight-percent water, 7 weight-percent Triton X-100, 3 weight-percent fragrance oil, 2 weight-percent ethanol, and 0.1 weight percent polyethylenimine.

Example 4

Determination of the Effect of pH on an Air-Freshener Composition of the Invention Air-freshener compositions were prepared according to the procedure described in Example 3, except that the pH of the crosslinker solution was modified. Table 3 shows the pH of the crosslinker solution, the time at which a substantial increase in viscosity was observed ($t_1$) and the gel time ($t_2$). Time $t_1$ can also be considered as the time at which the onset of polymerization could be observed.

TABLE 3

Effect of pH on an Air-Freshener Composition of the Invention

| pH | Gel Onset ($t_1$) (seconds) | Gel Time ($t_2$) (seconds) |
| --- | --- | --- |
| 8.5 | 210 | 300 |
| 8.7 | 130 | 180 |
| 9.0 | 60 | 80 |
| 10.0 | <3 | <3 |

These data show that the pH of a crosslinker solution that contains polyethylenimine (800 molecular weight) affects gel time and that the selection of pH of the composition can be used to optimize gel time.

Example 5

Effect of Amounts of Crosslinker on an Air-Freshener Composition of the Invention To determine the effect of crosslinker amount on an air-freshener composition of the invention, four air-freshener compositions were prepared using varying amounts of crosslinker for each composition.

The prepolymer of Example 1 was first prepared.

Next, a series of fragrance compositions was prepared by admixing 3 g fragrance oil (Berry Medley available from Wessel Fragrance Inc., Anglewood Cliff, N.J.), 2 g ethanol, 7 g Triton X-100 (available from Union Carbide Corporation), and varying amounts of water (depending on the amount of crosslinker solution added) in a 250 ml beaker using a magnetic stirrer until a clear solution was obtained and all components were dissolved. This took about 30 minutes. The prepolymer (3 g) was then added to these mixtures, and the components were mixed for an additional 4 minutes.

A 1 weight-percent crosslinker solution was prepared by dissolving 1 gram of polyethylenimine in 99 grams of water. The pH of the crosslinker solution was adjusted to about 9 by addition of concentrated hydrochloric acid. The crosslinker solution was then added to the mixture containing the prepolymer by adding varying amounts of the 1% polyethylenimine solution. All components were then mixed for about 15 seconds.

The compositions were evaluated by applying pressure to the surface of the composition with a probe. This evaluation was used to qualitatively determine the effect of crosslinker amount on the firmness of the compositions. Each composition was rated on a scale of 1 to 3, with 1 being very firm and 3 being less firm. The results are shown in Table 5.

TABLE 5

Effect of Crosslinker Amount on an Air-Freshener Composition of the Invention

| Sample No. | Water (grams) | PEI (1% solution) (grams) | PEI (weight percent) | Firmness |
| --- | --- | --- | --- | --- |
| 1 | 80 | 5 | 0.05 | 3 |
| 2 | 75 | 10 | 0.10 | 2 |
| 3 | 70 | 15 | 0.15 | 2 |
| 4 | 65 | 20 | 0.20 | 1 |

These data show that by altering the amount of polyethylenimine (800 molecular weight), while maintaining the amount of prepolymer constant, the gel firmness can be modified. The gel firmness increased as the amount of polyethylenimine increased. Generally a composition having a firmness of 3 has a higher number-average molecular weight between crosslinks than a composition having a firmness of 1.

Example 6

Preparation of an Air-Freshener Composition of the Invention Having a Gel Object Suspended Within the Composition A gel object was first prepared by making an air-freshener composition according to Example 3 except that 0.5 weight-percent water was replaced with 0.5 weight-percent green food coloring and the prepolymer was 5 weight percent instead of 3 weight percent. After the final mixing step, the mixture was dispensed into an object mold having a shape of a frog (1 inch by ¾ inch by ½ inch) and allowed to finish polymerizing for about 80 seconds. The object mold was a candy mold. After 30 minutes, the gel object was placed in a clear jar (200 ml).

An air-freshener composition for dispensing into the jar was then prepared. To prepare an air-freshener composition according to the invention, the prepolymer of Example 1 was first prepared.

Next, a fragrance composition was prepared by admixing 3 g fragrance oil (Berry Medley available from Wessel Fragrance Inc., Anglewood Cliff, N.J.), 2 g ethanol, 7 g TRITON X-100 (available from Union Carbide Corporation), and 75 g water in a 250 ml beaker using a mechanical stirrer until a clear solution was obtained and all components were dissolved. This took about 30 minutes. The prepolymer (2.5 g) was then added to this mixture, and the components were mixed for an additional 4 minutes.

A crosslinker solution was prepared by dissolving 1 weight percent of polyethylenimine in 100 grams of water. The pH of the crosslinker solution was adjusted to about 9 by adding concentrated hydrochloric acid. The crosslinker solution was then added to the mixture containing the prepolymer by adding 10 g of the 1% polyethylenimine solution. All components were then mixed for about 15 seconds and subsequently dispensed into the glass jar that contained the gel object. The gel time was about 80 seconds.

Example 7

Effect of Amounts of Crosslinker and Prepolymer on the Gel Strength of an Air-Freshener Composition of the Invention To determine the effect of crosslinker on the gel strength of an air-freshener composition of the invention, air-freshener compositions were prepared, and their gel strength was measured.

The prepolymer of Example 1 was first prepared.

Next, a fragrance composition was prepared by admixing 3 g fragrance oil (citrus Fresh, available from Flavor &

Fragrance Specialties, Mahwah, N.J.), 2 g Triton X-100 (Union Carbide Corporation, Danbury, Conn.), and varying amounts of water (depending on the amount of prepolymer and crosslinker added) in a 250 ml beaker using a magnetic stirrer until a clear solution was obtained and all components were dissolved. This took about 30 minutes. The prepolymer was then added to this mixture, and the components were mixed for an additional 4 minutes.

Crosslinker solutions (1 weight percent) were prepared by dissolving a water-soluble crosslinker (1 g) in water (99 g) and then adjusting the pH by addition of concentrated hydrochloric acid.

Air-freshener compositions were prepared by admixing all hydrogel components as described in Table 6. Generally all hydrogel components were admixed for about 15 seconds and then poured into a Bloom jar having an internal diameter of 59 mm, a height of 85 mm, and a capacity of 155 ml (available from Schott (Duran) and described in DIN 53260 (Deutsche Industrie Norm). The compositions were allowed to stand for 24 hours before any testing was done.

TABLE 6

Formulations of Air-Freshener Composition

| Component | Formulation 1 (weight percent) | Formulation 2* (weight percent) |
| --- | --- | --- |
| Water | 91.9 | 87.87 |
| Prepolymer | 3 | 7 |
| Polyethylenimine | 0.1 | 0.23 |
| Citrus Fresh | 3 | 3 |
| Triton X-100 | 2 | 2 |
| pH Polyethylenimine | 9 | 8 |

*Formulation 2 is not transparent according to the invention and is a comparative example.

The gel strength of each composition was determined using a Stevens Texture Analyzer and a 0.5-inch Bloom Gelometer plunger (both available from Stevens Company) as described in British Standard BS 757 (1975).

Formulation 1 showed a gel onset ($t_1$) of 35 seconds, a gel time ($t_2$) of 60 seconds (see Example 4 for description of $t_1$ and $t_2$), and a gel strength of 70 grams. Formulation 2 showed a gel onset ($t_1$) of 43 seconds, a gel time ($t_2$) of 72 seconds, and a gel strength of 370 grams.

Although the gel time was substantially the same for these Formulations, the results indicate that the gel strength substantially increased when the amounts of water-soluble crosslinker and prepolymer were increased.

Each composition was also evaluated for its percent transmittance about 24 hours after the hydrogel components were mixed. Each composition was evaluated using a cuvette having a path length of about 4 cm.

Figure 3:
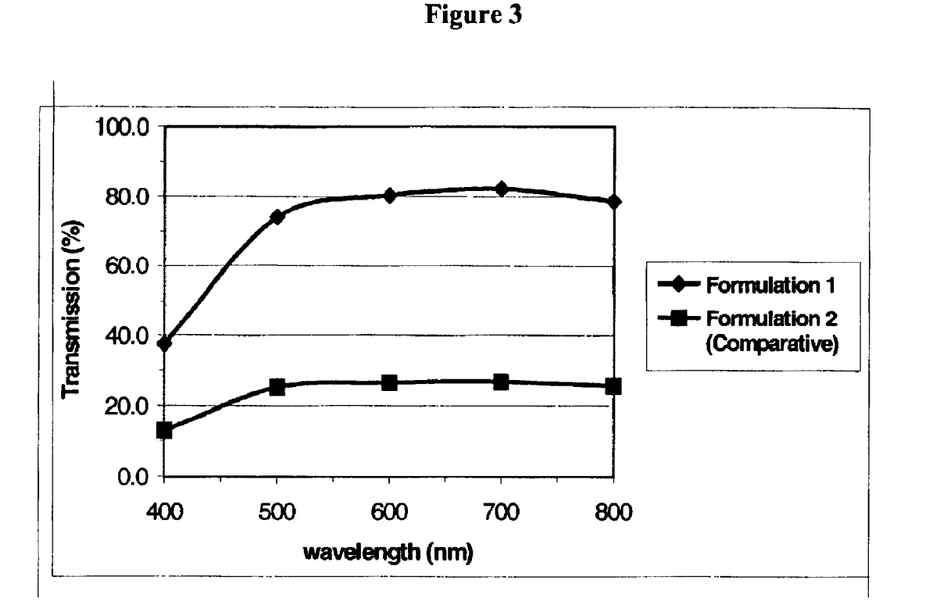
FIG. 3 shows the percent transmittance of a composition of the invention and a comparative composition over the visible range of 400 nm to 800 nm. The composition of the invention was prepared with 3 weight-percent prepolymer, and the comparative composition was prepared with 7 weight-percent prepolymer.

FIG. 3 shows the percent transmittance for Formulation 1 and Formulation 2. Formulation 1 showed a percent transmittance of about 80 percent at 600 nm, and Formulation 2 showed a percent transmittance of about 25 percent at 600 nm.

Although the gel strength of Formulation 2 can be desirable according to the invention, Formulation 2 is not transparent according to the invention, and, therefore, is a comparative example. These results suggest that the amounts of prepolymer and crosslinker used in Formulation 2 are ineffective to provide a transparent polyurethane hydrogel according to the invention.

Example 8

Effect of Amounts Crosslinker and Prepolymer on Evaporation of Moisture from a Polyurethane Hydrogel To determine the effect of crosslinker on the evaporation of moisture from a polyurethane hydrogel, polyurethane hydrogels were prepared, and the loss of moisture was measured.

The prepolymer of Example 1 was first prepared.

Next, crosslinker solutions (1 weight percent) were prepared by dissolving a water-soluble crosslinker (1 g) in water (99 g) and then adjusting the pH by addition of concentrated hydrochloric acid.

Polyurethane hydrogels were prepared by admixing components as described in Table 7. Generally all hydrogel components were admixed for about 15 seconds and then poured into Bloom jars as described in Example 7. The compositions were allowed to stand for 24 hours before any testing was done.

TABLE 7

Formulations of Polyurethane Hydrogels

| Component | Formulation 1 (weight percent) | Formulation 2 (weight percent) | Formulation 3 (weight percent) |
| --- | --- | --- | --- |
| Water | 96.9 | 94.83 | 92.87 |
| Prepolymer | 3 | 5 | 7 |
| Polyethylenimine | 0.1 | 0.17 | .23 |
| pH Polyethylenimine | 9.5 | 7.7 | 7.3 |

Each polyurethane hydrogel was weighed ($w_1$), and the gel strength was measured as described in Example 7.

Formulation 1 showed a gel onset ($t_1$) of 42 seconds, a gel time ($t_2$) of 82 seconds, and a gel strength of 53 grams. Formulation 2 showed a gel onset ($t_1$) of 58 seconds, a gel time ($t_2$) of 80 seconds, and a gel strength of 202 grams. Formulation 3 showed a gel onset ($t_1$) of 58 seconds, a gel time ($t_2$) of 78 seconds, and a gel strength of 327 grams.

These results show that gel times were substantially the same irrespective of amounts of water-soluble crosslinker and prepolymer but that gel strength increased as the amounts of water-soluble crosslinker and prepolymer increased.

The polyurethane hydrogels were allowed to stand at 20° C. and 50 relative humidity for 400 hours. The polyurethane hydrogels were then weighed again ($w_2$).

The percent loss of moisture ($w_2/w_1$)×100% was then determined for each Formulation. Formulation 1 lost about 63 weight percent, Formulation 2 lost about 54 weight percent, and Formulation 3 lost about 54 weight percent. Although these Formulations were not tested for percent transmissions, it is expected that Formulations 1 and 2 are transparent according to the invention and that Formulation 3 is not transparent according to the invention and, therefore, is a comparative example.

These results indicate that a polyurethane hydrogel having a higher gel strength loses moisture at a slower rate than does a polyurethane hydrogel having a lower gel strength. This can be useful to optimize fragrance release from an air-freshener composition. Generally it is not commercially desirable to have too rapid of fragrance release or too slow of fragrance release. One of skill in the art having read this specification can readily optimize fragrance release from an air-freshener composition.

Example 9
Preparation of a Polyurethane-Hydrogel Composition According to the Invention To investigate water-soluble crosslinkers useful according to the invention, two polyurethane-hydrogel compositions are prepared as follows.

The prepolymer solution is prepared by dissolving the prepolymer of Example 1 in water to a concentration of 2.5% (w/v).

Formulations are prepared by adding to the prepolymer solution 20 mM potassium-phosphate buffer, pH 8.0 and either polyoxyethylene bis(amine) (Sigma, catalog no. P-9906) (0.8% (w/v) (Formulation 1) (0.8% w/v) or a 3-arm amine end-capped polyethyleneglycol (Shearwater Corporation, Huntsville, Ala., catalog no. 0J2V0L13) (0.8% (w/v)) (Formulation 2). The components are mixed by inversion.

Formulation 1 and Formulation 2 are transparent.

What is claimed is:

1. A polyurethane-hydrogel composition, said composition being prepared by a method comprising:
   admixing at least one prepolymer and at least one water-soluble crosslinker in aqueous solvent and in the substantial absence of organic solvent to form a polyurethane-hydrogel mixture, said prepolymer being prepared from at least one water-soluble polyol and at least one isocyanate and being present in an amount of no greater than about 5 weight percent, said weight percent being based on total weight of all components; and
   (b) polymerizing said mixture to form a composition, wherein said composition is substantially polymerized, is transparent, has an effective number-average molecular weight between crosslinks and the crosslinker comprises an amine end-capped poly (ethylene oxide), or at least one of a 3-arm amine end-capped polyethyleneglycol or polyoxyethylene bis (amine).

2. A composition according to claim 1, wherein said crosslinker comprises an amine end-capped poly(ethylene oxide) crosslinker.

3. A composition according to claim 1, wherein said crosslinker comprises at least one of a 3-arm amine end-capped polyethyleneglycol and polyoxyethylene bis(amine).

4. A composition according to claim 1, wherein said water-soluble crosslinker comprises a polyamine, said polyamine having a charge density of at least 0.8 meq charge per gram of crosslinker.

5. A composition according to claim 1, wherein said crosslinker has a functionality effective to provide a reaction rate with said prepolymer that is at least 10 times faster than the reaction rate of water with said prepolymer.

6. A composition according to claim 1, wherein said prepolymar is prepared from an aliphatic or cycloaliphatic isocyanate.

7. A composition according to claim 6, wherein said isocyanate comprises isophorone diisocyanate.

8. A composition according to claim 1, wherein said prepolymer is prepared from a polyoxyalkylene polyol.

9. A composition according to claim 8, wherein said polyol comprises a 7,000 molecular-weight triol copolymer of 75% ethylene oxide and 25% propylene oxide.

10. A composition according to claim 1, wherein said prepolymer is prepared from an isocyanate comprising isophorone diisocyanate and a polyol comprising a 7,000 molecular-weight triol copolymer of 75% ethylene oxide and 25% propylene oxide.

11. A composition according to claim 1, wherein said mixture is formed by further admixing a fragrance composition with said at least one prepolymer and said at least one water-soluble crosslinker.

12. A composition according to claim 11, wherein said fragrance composition comprises a fragrance oil and a surfactant.

13. A composition according to claim 12, wherein said surfactant comprises at least one of ethoxylated alkyl phenol, nonylphenol, and ethoxylated alcohol.

14. A composition according to claim 1, wherein said mixture is formed by admixing at least one additive with said at least one prepolymer and said at least one water-soluble crosslinker.

15. An air-freshener composition, said composition being prepared by a method comprising:
   admixing at least one prepolymer, at least one water-soluble crosslinker, and at least one fragrance composition in aqueous solvent and in the substantial absence of organic solvent to form a polyurethane-hydrogel mixture, said prapolymer being prepared from at least one water-soluble polyol and at least one isocyanate and being present in an amount of no greater than about 5 weight percent, said weight percent being based on total weight of all components;
   (b) polymerizing said mixture to form a composition, wherein said composition is substantially polymerized, is transparent, and has an effective number-average molecular weight between crosslinks.

16. A composition according to claim 15, wherein said crosslinker comprises polyethylenimine.

17. A composition according to claim 15, wherein said crosslinker comprises an amine end-capped poly(ethylene oxide) crosslinker.

18. A composition according to claim 15, wherein said crosslinker comprise at least one of a 3-arm amine end-capped polyethyleneglycol and polyoxyethylene bis(amine).

19. A composition according to claim 15, wherein said water-soluble crosslinker comprises a polyamine, said polyamine having a charge density of at least 0.8 meq charge per gram of crosslinker.

20. A composition according to claim 15, wherein said prepolymer is prepared from an aliphatic or cycloaliphatic isocyanate.

21. A composition according to claim 20, wherein said isocyanate comprises isophorone diisocyanate.

22. A composition according to claim 15, wherein said prepolymer is prepared from a polyoxyalkylene polyol.

23. A composition according to claim 22, wherein said polyol comprises a 7,000 molecular-weight triol copolymer of 75% ethylene oxide and 25% propylene oxide.

24. A composition according to claim 15, wherein said prepolymer is prepared from an isocyanate comprising isophorone diisocyanate and a polyol comprising a 7,000 molecular-weight triol copolymer of 75% ethylene oxide and 25% propylene oxide.

25. A composition according to claim 15, wherein said fragrance composition comprises a fragrance oil.

26. A composition according to claim 24, wherein said fragrance composition further comprises at least one of a surfactant and an antifreeze.

27. A composition according to claim 26, wherein said surfactant comprises at least one of ethoxylated alkyl phenol, nonylphenol, and ethoxylated alcohol.

28. A composition according to claim 15, wherein said mixture is formed by admixing at least one additive with said at least one prepolymer and said at least one water-soluble crosslinker.

29. An air freshener, said air freshener comprising
(a) a container; and
a polyurethane-hydrogel composition dispensed into said container, said composition being prepared by a method comprising:
admixing at least one prepolymer, at least one water-soluble crosslinker, and at least one fragrance composition in aqueous solvent and in the substantial absence of organic solvent to form a polyurethane-hydrogel mixture, said prepolymer being prepared from at least one water-soluble polyol and at least one isocyanate and being present in an amount of no greater than about 5 weight percent, said weight percent being based on total weight of all components; and
(ii) polymerizing said mixture in said container to form an air freshener, wherein said air freshener is substantially polymerized, is transparent, and has an effective number-average molecular weight between crosslinks.

30. An air freshener according to claim 29, wherein said crosslinker comprises polyethylenimine.

31. An air freshener according to claim 29, wherein said crosslinker comprises an amine end-capped poly(ethylene oxide) crosslinker.

32. An air freshener according to claim 29, wherein said crosslinker comprises at least one of a 3-arm amine end-capped polyethyleneglycol and polyoxyethylene bis(amine).

33. An air freshener according to claim 29, wherein said water-soluble crosslinker comprises a polyamine, said polyamine having a charge density of at least 0.8 meq charge per gram of crosslinker.

34. An air freshener according to claim 29, wherein said prepolymer is prepared from an aliphatic or cycloaliphatic isocyanate.

35. An air freshener according to claim 34, wherein said isocyanate comprises isophorone diisocyanate.

36. An air freshener according to claim 29, wherein said prepolymer is prepared from a polyoxyalkylene polyol.

37. An air freshener according to claim 36, wherein said polyol comprises a 7,000 molecular-weight triol copolymer of 75% ethylene oxide and 25% propylene oxide.

38. An air freshener according to claim 29, wherein said prepolymer is prepared from an isocyanate comprising isophorone diisocyanate and a polyol comprising a 7,000 molecular-weight triol copolymer of 75% ethylene oxide and 25% propylene oxide.

39. An air freshener according to claim 29, wherein said fragrance composition comprises a fragrance oil.

40. An air freshener according to claim 39, wherein said fragrance composition further comprises at least one of a surfactant and an antifreeze.

41. An air freshener according to claim 29, wherein said composition further comprises a gel object suspended within said composition.

42. An air freshener according to claim 29, wherein said mixture is formed by further admixing a colorant with said prepolymer and said water-soluble crosslinker.

43. A method for preparing a transparent polyurethane-hydrogel composition, said method comprising:
admixing at least one prepolymer and at least one water-soluble crosslinker in aqueuos solvent and in the substantial absence of organic solvent to form a polyurethane-hydrogel mixture, said prepolymer comprising at least one water-soluble polyol and at least one isocyanate and being present in an amount of no greater than about 5 weight percent, said weight percent being based on total weight of all components; wherein the crosslinker comprises an amine end-capped poly (ethylene oxide), or at least one of a 3-arm amine end-capped polyethyleneglycol or polyoxyethylene bis (amine) and
(b) polymnerizing said mixture to form a composition, wherein said composition is substantially polymerized, is transparent, and has an effective number-average molecular weight between crosslinks.

44. A method according to claim 43, wherein said crosslinker comprises an amine end-capped poly(ethylene oxide) crosslinker.

45. A method according to claim 43, wherein said crosslinker comprises at least one of a 3-arm amine end-capped polyethyleneglycol and polyoxyethylene bis(amine).

46. A method according to claim 43, wherein said water-soluble crosslinker comprises a polyamine, said polyamine having a charge density of at least 0.8 meq charge per gram of crosslinker.

47. A method according to claim 43, wherein said prepolymer is prepared from an aliphatic or cycloaliphatic isocyanate.

48. A method according to claim 47, wherein said isocyanate comprises isophorone diisocyanate.

49. A method according to claim 43, wherein said prepolymer is prepared from a polyoxyalkylene polyol.

50. A method according to claim 49, wherein said polyol comprises a 7,000 molecular-weight triol copolymer of 75% ethylene oxide and 25% propylene oxide.

51. A method according to claim 43, wherein said prepolymer is prepared from an isocyanate comprising isophorone diisocyanate and a polyol comprising a 7,000 molecular-weight triol copolymer of 75% ethylene oxide and 25% propylene oxide.

* * * * *